US008569002B2

(12) United States Patent
Lum et al.

(10) Patent No.: US 8,569,002 B2
(45) Date of Patent: Oct. 29, 2013

(54) MULTIPLEXED LUCIFERASE REPORTER ASSAY SYSTEMS

(75) Inventors: Lawrence Lum, Dallas, TX (US); Ozlem Kulak, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 320 days.

(21) Appl. No.: 12/908,754

(22) Filed: Oct. 20, 2010

(65) Prior Publication Data

US 2012/0102581 A1    Apr. 26, 2012

(51) Int. Cl.
*C12Q 1/66* (2006.01)
*C12Q 1/68* (2006.01)
*G01N 33/567* (2006.01)

(52) U.S. Cl.
USPC .............................. 435/8; 435/6.1; 435/7.21

(58) Field of Classification Search
USPC ............................................................ 435/8
See application file for complete search history.

(56) References Cited

U.S. PATENT DOCUMENTS

| 5,814,471 | A  | 9/1998  | Wood .............................. | 435/8  |
| 7,601,846 | B2 | 10/2009 | Cottam et al. ................ | 548/151 |

FOREIGN PATENT DOCUMENTS

| JP | 2001048786 | 2/2001 |
| WO | WO 02/14321 | 2/2002 |

OTHER PUBLICATIONS

"BioLux™ *Cyprodina* Luciferase Assay Kit: Instruction Manual E3309" New England BioLabs, Ipswich, MA, Dec. 2009.
"BioLux™ *Gaussia* Luciferase Assay Kit: Instruction Manual E3300" New England BioLabs, Ipswich, MA, Nov. 2009.
Angelopoulos et al., "Bayseian model averaging for ligand discovery," *Journal of Chemical Information and Modeling*, 49(6):1547-1557, 2009.
Barchechath et al., "Inhibitors of apoptosis in lymphocytes: Synthesis and biological evaluation of compounds related to pifithrin-α," *Journal of Medicinal Chemistry*, 48(20):6409-6422, 2005.
El-shorbagi et al., "Imidazo[2,1-b]benzothiazoles. I.," *Chemical & Pharmaceutical Bulletin*, 36(12):4760-8, 1988.
Ei-Shorbagi et al., "Imidazo[2,1-b]benzothiazoles. II. Synthesis and anti-inflammatory activity of some imidazol[2,1-b]benzothiazoles," *Chemical & Pharmaceutical Bulletin*, 37(11):2971-5, 1989.
Grin et al., "Investigations in the imidazole series: Reaction of 2-aminobenzothiazoles with α—halo ketones," *Chemistry of Heterocyclic Compounds*, 9:1149-1152, 1972.
Jones and Stanforth, "ChemInform Abstract: The Vilsmeier Reaction of Fully Conjugated Carbocycles and Heterocycles," *ChemInform*, 28: No. doi: 10.1002/chin.199715268, 1997.
Mase and Murase, "Nucleophilic substitution reactions on sulfur by n-butyllithium 2," *Heterocycles*, 26:3159-3164, 1987.
Mase et al., "Imidazo[2,1-b]benzothiazoles. 2. New immunosuppressive agents," *Journal of Medicinal Chemistry*, 29(3):386-94, 1986.
Mase et al., "Nucleophilic substitution reactions on sulfur by n-butyllithium. 2.," *Heterocycles*, 26(12):3159-64, 1987.
Scifinder; Chemical Abstracts Service: Columbus, OH, 2010, RN 1188029-32-4 (accessed Aug. 13, 2010).
Scifinder; Chemical Abstracts Service: Columbus, OH, 2010, RN 1188215-75-9(accessed Aug. 13, 2010), calculated using ACD/Labs software version 11.02 1994-2010.
Scifinder; Chemical Abstracts Service: Columbus, OH, 2010, RN 1188215-85-1 (accessed Aug. 13, 2010), calculated using ACD/Labs software version 11.02 1994-2010.
Scifinder; Chemical Abstracts Service: Columbus, OH, 2010, RN 1188029-25-5 (accessed Aug. 13, 2010).
Scifinder; Chemical Abstracts Service: Columbus, OH, 2010, RN 1188217-51-7 (accessed Aug. 13, 2010), calculated using ACD/Labs software version 11.02 1994-2010.
Scifinder; Chemical Abstracts Service: Columbus, OH, 2010, RN 1188217-64-2 (accessed Aug. 13, 2010), calculated using ACD/Labs software version 11.02 1994-2010.
Scifinder; Chemical Abstracts Service: Columbus, OH, 2010, RN 24247-14-1 (accessed Aug. 13, 2010).
Scifinder; Chemical Abstracts Service: Columbus, OH, 2010, RN 352200-23-8 (accessed Aug. 13, 2010).
Scifinder; Chemical Abstracts Service: Columbus, OH, 2010, RN 38956-27-3 (accessed Aug. 13, 2010), calculated using ACD/Labs software version 11.02 1994-2010.
Scifinder; Chemical Abstracts Service: Columbus, OH, 2010, RN 419557-50-9 (accessed Aug. 13, 2010), calculated using ACD/Labs software version 11.02 1994-2010.
Scifinder; Chemical Abstracts Service: Columbus, OH, 2010, RN 7178-23-6 (accessed Aug. 13, 2010), calculated using ACD/Labs software version 11.02 1994-2010.
Scifinder; Chemical Abstracts Service: Columbus, OH, 2010, RN 940394-25-2 (accessed Aug. 13, 2010), calculated using ACD/Labs software version 11.02 1994-2010.
Scifinder; Chemical Abstracts Service: Columbus, OH, 2010, RN 940438-95-9 (accessed Aug. 13, 2010), calculated using ACD/Labs software version 11.02 1994-2010.

*Primary Examiner* — Valarie Bertoglio
(74) *Attorney, Agent, or Firm* — Parker Highlander PLLC

(57) ABSTRACT

Inhibitors of luciferase enzymes are disclosed and find use in multiplexed assays using multiple luciferases and multiple inhibitors, in both in vitro and in vivo embodiments.

18 Claims, 6 Drawing Sheets

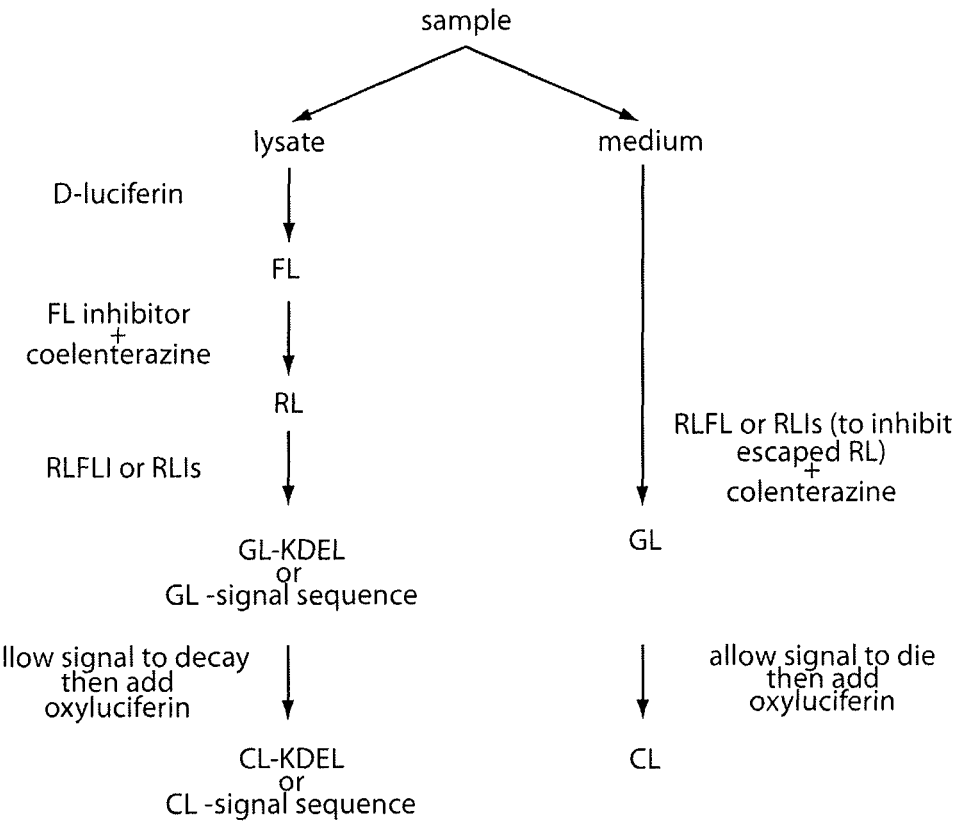

FL: firefly luciferase (cytoplasmic)
RL: Renilla luciferase (cytoplasmic
GL: Gaussia luciferase (secreted)
GL-KDEL: Gaussia luciferase with ER retention signal
GL--signal sequence: Gaussia luciferase expressed in cytoplasm
CL: Cypridina luciferase (secreted)
CL-KDEL: Cypridina luciferase with ER retention signal
CL--signal sequence: Cypridina luciferase expressed in cytoplasm
coelenterazine: substrate for RL and GL
luciferin: substrate for FL
oxyluciferin: substrate for CL

FIG. 5

MULTIPLEXED LUCIFERASE REPORTER ASSAY SYSTEMS

STATEMENT REGARDING FEDERALLY SPONSORED RESEARCH OR DEVELOPMENT

This invention was made in part with government support under Grant No. 1R01GM076398 from the National Institutes of Health. The United States Government has certain rights in the invention.

TECHNICAL FIELD

The present invention relates to the fields of molecular biology, biochemistry, and drug screening. More particularly, the present invention relates to the use of multiple luciferases and multiple inhibitors thereof to create a multiplexed system permitting analysis of multiple targets at the same time and in sequence.

BACKGROUND OF THE INVENTION

Reporter genes have become an invaluable tool in studies of gene expression. They are widely used in biomedical and pharmaceutical research and also in molecular biology and biochemistry. A key feature in reporter assays is an expression cassette comprising a coding region for marker of interest and a transcriptional regulatory region, i.e., a promoter regulatory region, that drives expression of the reporter. Any agent can then be tested for direct or indirect effects on the promoter, thereby identifying agents with potential value in directing control of products naturally driven by the promoter regulatory region. Common reporters are β-galactosidase, β-glucuronidase and luciferase, which rely upon various readouts including luminescence, absorbance and fluorescence.

Luciferase is a generic term for the class of oxidative enzymes used in bioluminescence and is distinct from a photoprotein. The name is derived from Lucifer, the root of which means "light-bearer." The advantages of a luciferase assay are the high sensitivity, the absence of luciferase activity inside most of the cell types, the wide dynamic range, rapidity and low costs. One example is the firefly luciferase from the firefly *Photinus pyralis*, and this protein requires no post-translational modification for enzyme activity; it is not even toxic in high concentration (in vivo) and can be used in pro- and eukaryotic cells. Firefly luciferase catalyzes the bioluminescent oxidation of the luciferin in the presence of ATP, magnesium and oxygen.

In many assay formats, it is useful to examine multiple effects using distinct reporter cassettes. This is termed "multiplexing," i.e., using multiple readouts to simultaneous assess various effects. By using multiplexed assays, one can acquire information much more quickly. While there exist different luciferase enzymes, current assays only permit looking at two different reporters within the confines of a single assay. Thus, there remains a need to develop reagents that permit higher levels of multiplex luciferase assays.

SUMMARY OF THE INVENTION

Thus, in accordance with the present invention, there is provided a method of detecting a plurality of distinct luciferase molecules comprising (a) providing a plurality of distinct luciferase molecules and substrates therefor; (b) providing a plurality of distinct luciferase inhibitors, wherein the plurality of inhibitors inhibit at least two of the plurality of distinct luciferase molecules; (c) sequentially measuring chemiluminescence from each of the plurality of distinct luciferase molecules, wherein other of the plurality of the distinct luciferase molecules are inhibited or lack substrate. The plurality of distinct luciferase molecules may be provided sequentially or simultaneously. The plurality of distinct luciferase molecules may comprise 2, 3, 4, 5 or 6 distinct luciferase molecules. The plurality of distinct luciferase inhibitors may comprise 2, 3, or 4 distinct luciferase inhibitors.

The plurality of distinct luciferase molecules may comprise two or more or each of firefly luciferase, *renilla* luciferase, gaussia luciferase, *cypridina* luciferase, gaussia luciferase lacking a secretion signal sequence or having an endoplasmic retention sequence, or *cypridina* luciferase lacking a secretion signal sequence or having an endoplasmic retention sequence. The plurality of luciferases may be expressed from cells in culture. The method may further comprise separating the cells from cell medium, such as by disrupting the cells to form a cell lysate.

The substrates may comprise two or all three of D-luciferin, oxyluciferin, and coelenterazine. The inhibitor may be selective or specific for *renilla* luciferase, such as:

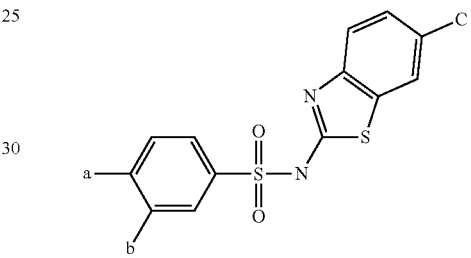

wherein a is substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide, b is H, substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide, and c is H, substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide. Alternatively, the inhibitor may be selective or specific for firefly luciferase, such as:

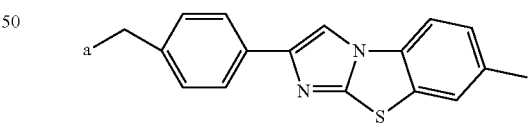

wherein a is H, substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide. The inhibitor may be cross-reactive with *renilla* luciferase and firefly luciferase.

In another embodiment, there is provided a biological system comprising (a) a plurality of distinct luciferase molecules and substrates therefor; and (b) a plurality of distinct luciferase inhibitors, wherein the plurality of inhibitors inhibit at least two of the plurality of distinct luciferase molecules. The plurality of distinct luciferase molecules may comprise 2, 3, 4, 5 or 6 distinct luciferase molecules. The plurality of distinct luciferase inhibitors may comprise 2, 3, or 4 distinct luciferase inhibitors. The plurality of distinct luciferase molecules comprises two or more or each of firefly luciferase, *renilla* luciferase, gaussia luciferase, *cypridina* luciferase, gaussia luciferase lacking a secretion signal sequence or having an endoplasmic retention sequence, or *cypridina* luciferase lacking a secretion signal sequence or having an endoplasmic retention sequence.

The system may further comprise cells that express the plurality of luciferase molecules. The substrates may comprise two or all three of D-luciferin, oxyluciferin, and coelenterazine. The inhibitor may be selective or specific for *renilla* luciferase, such as:

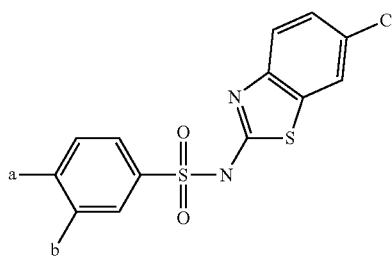

wherein a is substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide, b is H, substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide, and c is H, substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide. Alternatively, the inhibitor may be selective or specific for firefly luciferase, such as:

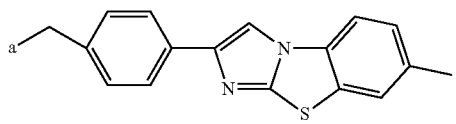

wherein a is H, substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide. The inhibitor may be cross-reactive with *renilla* luciferase and firefly luciferase.

In yet another embodiment, there is provided a kit comprising (a) a plurality of distinct luciferase substrates; and (b) a plurality of distinct luciferase inhibitors. The plurality of distinct luciferase substrates may comprise D-luciferin, oxyluciferin, and coelenterazine. The plurality of distinct luciferase inhibitors may comprise inhibitors for firefly luciferase and *renilla* luciferase. The kit may further comprise cells for expression of luciferase molecules. The kit may further comprise a plurality of expression constructs comprising sequences for expressing a plurality of luciferase molecules.

In a further embodiment, there is provided a method of imaging a cell in vivo comprising (a) providing a non-human animal comprising a cell expressing a plurality of distinct luciferase molecules; (b) providing to the animal (i) luciferase substrates; and (ii) a plurality of distinct luciferase inhibitors, wherein the plurality of inhibitors inhibit at least two of the plurality of distinct luciferase molecules; (c) sequentially measuring chemiluminescence from each of the plurality of distinct luciferase molecules, wherein other of the plurality of the distinct luciferase molecules are inhibited or lack substrate. The cell may be a cancer cell. The plurality of distinct luciferase molecules may be provided sequentially or simultaneously. The plurality of distinct luciferase molecules may comprise 2, 3, 4, 5 or 6 distinct luciferase molecules. The plurality of distinct luciferase inhibitors may comprise 2, 3, or 4 distinct luciferase inhibitors.

The plurality of distinct luciferase molecules may comprise two or more or each of firefly luciferase, *renilla* luciferase, gaussia luciferase, *cypridina* luciferase, gaussia luciferase lacking a secretion signal sequence or having an endoplasmic retention sequence, or *cypridina* luciferase lacking a secretion signal sequence or having an endoplasmic retention sequence. The substrates may comprise two or all three of D-luciferin, oxyluciferin, and coelenterazine. The inhibitor may be selective or specific for *renilla* luciferase, such as:

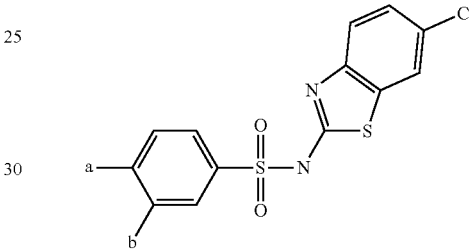

wherein a is substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide, b is H, substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide, and c is H, substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide. Alternatively, the inhibitor may be selective or specific for firefly luciferase, such as:

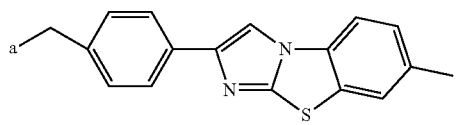

wherein a is H, substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide. The inhibitor may be cross-reactive with *renilla* luciferase and firefly luciferase.

Providing may comprise introducing into the non-human animal a cell previously transfected or transformed with one or more expression cassettes comprising one or more promoters driving the plurality of luciferase molecules, such as into a cancer cell. Providing may also comprise use of a transgenic non-human animal generated from stem cells transfected or transformed with one or more expression cassettes comprising one or more promoters driving the plurality of luciferase molecules. Providing may alternatively comprise transfecting or transforming a cell of the non-human animal in vivo with one or more expression cassettes comprising one or more promoters driving the plurality of luciferase molecules, such as by transfecting or transforming with viral infection of the non-human animal.

The method may further comprise providing to the non-human animal a candidate substance, for example, wherein step (c) is performed after provision of the candidate substance, or wherein step (c) is performed before provision of the candidate substance, and further comprising, after provision of the candidate substance, sequentially measuring chemiluminescence from each of the plurality of distinct luciferase molecules, wherein other of the plurality of the distinct luciferase molecules are inhibited or lack substrate. The non-human animal may be a mouse.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Schematic of two screens using the UTSW chemical library to identify firefly luciferase (FLuc) and *Renilla* luciferase (RLuc) inhibitors. (FIG. 1B) Cell lines used in various screening steps of the screens. (FIG. 1C) Structure and in vitro IC50 of firefly luciferase inhibitors 1 and 2 (FLI1 and FLI2). (FIG. 1D) Structure and in vitro IC50 of *Renilla* luciferase inhibitor 1 (RLI1).

(FIG. 3B) A general scaffold that supports specific FLuc inhibitory activity is shown.

FIG. 5. A general schematic for conducting multi-luciferase assays using FLIs, RLFL, and RLIs.

DETAILED DESCRIPTION OF THE INVENTION

I. DEFINITIONS

Figure 1:
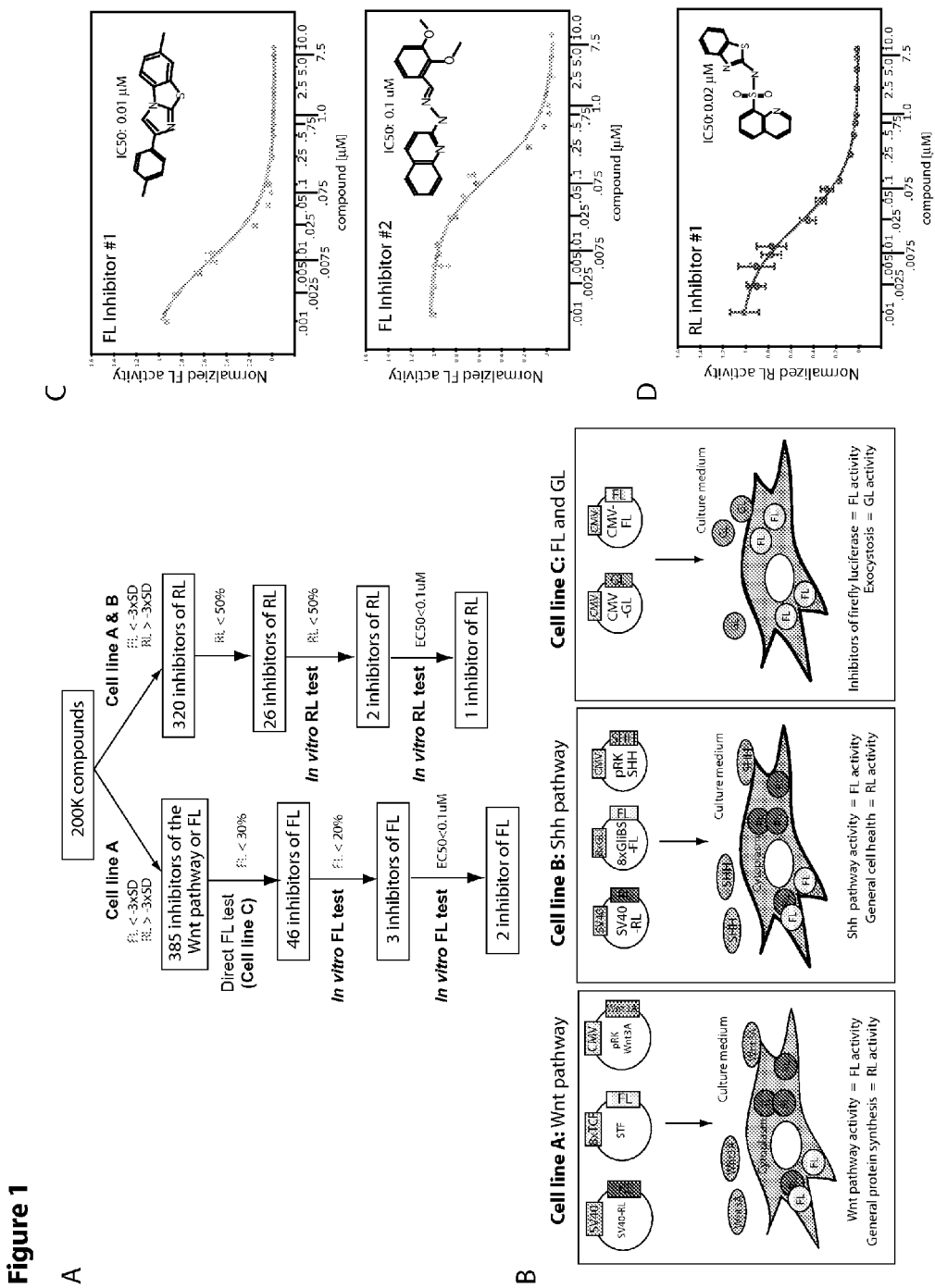
FIGS. 1A-D. Identification of FL and RL inhibitors from high-throughput chemical library screens.

Unless defined otherwise, technical and scientific terms used herein have the same meaning as commonly understood by one of ordinary skill in the art to which this invention belongs. For purposes of the present invention, the following terms are defined below.

An inhibitor is defined as a molecule that is able to reduce the activity of a luciferase molecule to no more than about 20% of the normal activity level, as measured in a similar assay without the inhibitor.

A selective inhibitor is one that inhibits a particular luciferase by at least X-fold over any other luciferase, or one that has less than Y % inhibition of any other luciferase.

A specific inhibitor is one that inhibits a particular luciferase by at least Z-fold over any other luciferase, or one that has less than Y % inhibition of any other luciferase.

When used in the context of a chemical group, "hydrogen" means —H; "hydroxy" means —OH; "oxo" means =O; "halo" means independently —F, —Cl, —Br or —I; "amino" means —NH$_2$ (see below for definitions of groups containing the term amino, e.g., alkylamino); "hydroxyamino" means —NHOH; "nitro" means —NO$_2$; imino means =NH (see below for definitions of groups containing the term imino, e.g., alkylimino); "cyano" means —CN; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; "thio" means =S; "thioether" means —S—; "sulfonamido" means —NHS(O)$_2$— (see below for definitions of groups containing the term sulfonamido, e.g., alkylsulfonamido); "sulfonyl" means —S(O)$_2$— (see below for definitions of groups containing the term sulfonyl, e.g., alkylsulfonyl); "sulfinyl" means —S(O)— (see below for definitions of groups containing the term sulfinyl, e.g., alkylsulfinyl); and "silyl" means —SiH$_3$ (see below for definitions of group(s) containing the term silyl, e.g., alkylsilyl).

The term "amido" (acylamino), when used without the "substituted" modifier, refers to the group —NHR, in which R is acyl, as that term is defined above. A non-limiting example of an acylamino group is —NHC(O)CH$_3$. When the term amido is used with the "substituted" modifier, it refers to groups, defined as —NHR, in which R is substituted acyl, as that term is defined above. The groups —NHC(O)OCH$_3$ and —NHC(O)NHCH$_3$ are non-limiting examples of substituted amido groups.

The term "alkyl" when used without the "substituted" modifier refers to a non-aromatic monovalent group with a saturated carbon atom as the point of attachment, a linear or branched, cyclo, cyclic or acyclic structure, no carbon-carbon double or triple bonds, and no atoms other than carbon and hydrogen. The groups, —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "substituted alkyl" refers to a non-aromatic monovalent group with a saturated carbon atom as the point of attachment, a linear or branched, cyclo, cyclic or acyclic structure, no carbon-carbon double or triple bonds, and at least one atom independently selected from the group consisting of N, O, F, Cl, Br, I, Si, P, and S. The following groups are non-limiting examples of substituted alkyl groups: —CH$_2$OH, —CH$_2$Cl, —CH$_2$Br, —CH$_2$SH, —CF$_3$, —CH$_2$CN, —CH$_2$C(O)H, —CH$_2$C(O)OH, —CH$_2$C(O)OCH$_3$, —CH$_2$C(O)NH$_2$, —CH$_2$C(O)NHCH$_3$, —CH$_2$C(O)CH$_3$, —CH$_2$OCH$_3$, —CH$_2$OCH$_2$CF$_3$, —CH$_2$OC(O)CH$_3$, —CH$_2$NH$_2$, —CH$_2$NHCH$_3$, —CH$_2$N(CH$_3$)$_2$, —CH$_2$CH$_2$Cl, —CH$_2$CH$_2$OH, —CH$_2$CF$_3$, —CH$_2$CH$_2$OC(O)CH$_3$, —CH$_2$CH$_2$NHCO$_2$C(CH$_3$)$_3$, and —CH$_2$Si(CH$_3$)$_3$.

The term "alkenyl" when used without the "substituted" modifier refers to a monovalent group with a nonaromatic carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "substituted alkenyl" refers to a monovalent group with a nonaromatic carbon atom as the point of attachment, at least one nonaromatic carbon-carbon double bond, no carbon-carbon triple bonds, a linear or branched, cyclo, cyclic or acyclic structure, and at least one atom independently selected from the group consisting of N, O, F, Cl, Br, I, Si, P, and S. The groups, —CH=CHF, —CH=CHCl and —CH=CHBr, are non-limiting examples of substituted alkenyl groups.

The term "alkynyl" when used without the "substituted" modifier refers to a monovalent group with a nonaromatic carbon atom as the point of attachment, a linear or branched, cyclo, cyclic or acyclic structure, at least one carbon-carbon triple bond, and no atoms other than carbon and hydrogen. The groups, —C≡CH, —C≡CCH$_3$, —C≡CC$_6$H$_5$ and —CH$_2$C≡CCH$_3$, are non-limiting examples of alkynyl groups. The term "substituted alkynyl" refers to a monovalent group with a nonaromatic carbon atom as the point of attachment and at least one carbon-carbon triple bond, a linear or branched, cyclo, cyclic or acyclic structure, and at least one atom independently selected from the group consisting of N, O, F, Cl, Br, I, Si, P, and S. The group, —C≡CSi(CH$_3$)$_3$, is a non-limiting example of a substituted alkynyl group.

The term "alkoxy" when used without the "substituted" modifier refers to the group —OR, in which R is an alkyl, as that term is defined above. Non-limiting examples of alkoxy groups include: —OCH$_3$, —OCH$_2$CH$_3$, —OCH$_2$CH$_2$CH$_3$, —OCH(CH$_3$)$_2$, —OCH(CH$_2$)$_2$, —O— cyclopentyl, and —O— cyclohexyl. The term "substituted alkoxy" refers to the group —OR, in which R is a substituted alkyl, as that term is defined above. For example, —OCH$_2$CF$_3$ is a substituted alkoxy group.

II. LUCIFERASES

Luciferase is a generic term for the class of oxidative enzymes used in bioluminescence and is distinct from a photoprotein. One famous example is the firefly luciferase from *Photinus pyralis*. "Firefly luciferase" as a laboratory reagent usually refers to *P. pyralis* luciferase, although recombinant luciferases from several other species of fireflies are also commercially available.

In luminescent reactions, light is produced by the oxidation of a luciferin (a pigment):

The most common luminescent reactions release CO$_2$ as a product. The rates of this reaction between luciferin and oxygen are extremely slow until they are catalyzed by luciferase, sometimes mediated by the presence of cofactors such as calcium ions or ATP. The reaction catalyzed by firefly luciferase takes place in two steps:

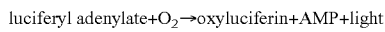

The reaction is very energetically efficient: nearly all of the energy input into the reaction is transformed into light. As a comparison, the incandescent light bulb loses about 90% of its energy to heat. Photon emission can be detected by light sensitive apparatus such as a luminometer or modified optical microscopes. This allows observation of biological processes.

A subtle structural difference in luciferase has been discovered to be the cause of the change in bioluminescence emission color from a yellow-green to red. The structure of wild-type luciferase and red mutant (S286N) luciferase from the Japanese Genji-Botaru (*Luciola cruciata*) in complex with an intermediate analogue 5'-O—[N-(dehydroluciferyl)-sulfamoyl]adenosine (DLSA) was examined and studies showed that the wild-type luciferase complexed with DLSA exhibited a 'closed form' of the active site, where the side chain of amino acid isoleucine 288 moved towards the benzothiazole ring of DLSA, creating a rigid hydrophobic pocket. The 'closed form' wild-type luciferase bound the excited state of oxyluciferin in a highly rigid and nonpolar microenvironment, minimizing energy loss before emitting yellow-green light. The S286N luciferase complexed with DLSA exhibited an 'open form' of the active site, where the amino acid side chain of isoleucine 288 did not move towards the benzothiazole ring of DLSA, creating a less rigid and less hydrophobic microenvironment. The 'open form' S286N luciferase had a less rigid microenvironment allowing some energy loss from the excited state of oxyluciferin, which resulted in the emission of low-energy red light.

A variety of organisms regulate their light production using different luciferases in a variety of light-emitting reactions. The most famous are the fireflies, although the enzyme exists in organisms as different as the Jack-O-Lantern mushroom (*Omphalotus olearius*) and many marine creatures. In fireflies, the oxygen required is supplied through a tube in the abdomen called the abdominal trachea. The luciferases of fireflies, of which there are over 2000 species, and of the Elateroidea (fireflies, click beetles and relatives) in general, are diverse enough to be useful in molecular phylogeny. The most thoroughly studied luciferase is that of the Photinini firefly *Photinus pyralis*, which has an optimum pH of 7.8.

Also well studied is the luciferase from *Renilla reniformis*. In this organism, the luciferase is closely associated with a luciferin-binding protein as well as a green fluorescent protein (GFP). Calcium triggers release of the luciferin (coelenterazine) from the luciferin binding protein. The substrate is then available for oxidation by the luciferase, where it is degraded to coelenteramine with a resultant release of energy. In the absence of GFP, this energy would be released as a photon of blue light (peak emission wavelength 482 nm). However, due to the closely associated GFP, the energy released by the luciferase is instead coupled through resonance energy transfer to the fluorophore of the GFP, and is subsequently released as a photon of green light (peak emission wavelength 510 nm). The catalyzed reaction is:

coelenterazine+$O_2$→coelenteramine+$CO_2$+photon of light

Newer luciferases have recently been identified that, unlike *Renilla* or Firefly luciferase, are naturally secreted molecules. One such example is the *Metridia* luciferase (MetLuc) that is derived from the marine copepod *Metridia longa*. The *M. longa* secreted luciferase gene encodes a 24 kDa protein containing an N-terminal secretory signal peptide of 17 amino acid residues. The sensitivity and high signal intensity of this luciferase molecule proves advantageous in many reporter studies. Some of the benefits of using a secreted reporter molecule like MetLuc is its no-lysis protocol that allows one to be able to conduct live cell assays and multiple assays on the same cell.

Gaussia luciferase (GLuc) is a 20 kDa luciferase from the marine cocepod *Gaussia princeps*. This luciferase, which does not require ATP, catalyzes the oxidation of the substrate coelenterazine in a reaction that produces light (480 nm), and has considerable advantages over other luminescent reporter genes. It is normally secreted from the cells and its secretion signal also functions very efficiently in mammalian cells. GLuc offers the advantage of a greatly increased bioluminescent signal relative to the commonly used firefly (Fluc) and *Renilla* luciferases (RLuc). GLuc was determined to emit light with a specific activity of $4.2 \times 10^{24}$ photons/s/mol, the highest reported activity for any characterized luciferase.

*Cypridina* luciferase (CLuc) is isolated from the marine ostracod *Cypridina noctiluca* and is efficiently secreted from mammalian cells. CLuc differs from Fluc in the form of luciferin it uses as a substrate (*Cypridina* luciferin), it its independence from ATP to achieve light emission. CLuc does not react with coelenterazine, a common substrate of marine luciferases. This allows the simultaneous detection of both of FLuc, Rluc, or GLuc with CLuc expressed from the same cells provided the cell-derived samples can be divided and independently analyzed for each enzymatic activity, or if a method for sequentially measuring individual enzymatic activities from the same cell-derived sample is in place.

Luciferase can be produced in the lab through genetic engineering for a number of purposes. Luciferase genes can be synthesized and inserted into organisms or transfected into cells. Mice, silkworms, and potatoes are just a few organisms that have already been engineered to produce the protein. In biological research, luciferase commonly is used as a reporter to assess the transcriptional activity in cells that are transfected with a genetic construct containing the luciferase gene under the control of a promoter of interest. Luciferase can also be used to detect the level of cellular ATP in cell viability assays or for kinase activity assays. Additionally, pro-luminescent molecules that are converted to luciferin upon activity of a particular enzyme can be used to detect enzyme activity in coupled or two-step luciferase assays. Such substrates have been used to detect caspase activity and cytochrome P450 activity, among others.

Whole animal imaging (referred to as in vivo or, occasionally, ex vivo imaging) is a powerful technique for studying cell populations in live animals, such as mice. Different types of cells (e.g., bone marrow stem cells, T-cells) can be engineered to express a luciferase allowing their non-invasive visualization inside a live animal using a sensitive charge-couple device camera (CCD camera). This technique has been used to follow tumorigenesis and response of tumors to treatment in animal models. However, environmental factors and therapeutic interferences may cause some discrepancies between tumor burden and bioluminescence intensity in relation to changes in proliferative activity. The intensity of the signal measured by in vivo imaging may depend on various factors, such as D-luciferin absorption through the peritoneum, blood flow, cell membrane permeability, availability of co-factors, intracellular pH and transparency of overlying tissue, in addition to the amount of luciferase.

Luciferase can be used in blood banks to determine if red blood cells are starting to break down. Forensic investigators can use a dilute solution containing the enzyme to uncover traces of blood remaining on surfaces at a crime scene. Luciferase is a heat sensitive protein that is used in studies on protein denaturation, testing the protective capacities of heat shock proteins. The opportunities for using luciferase continue to expand.

III. LUCIFERASE INHIBITORS

Figure 2:
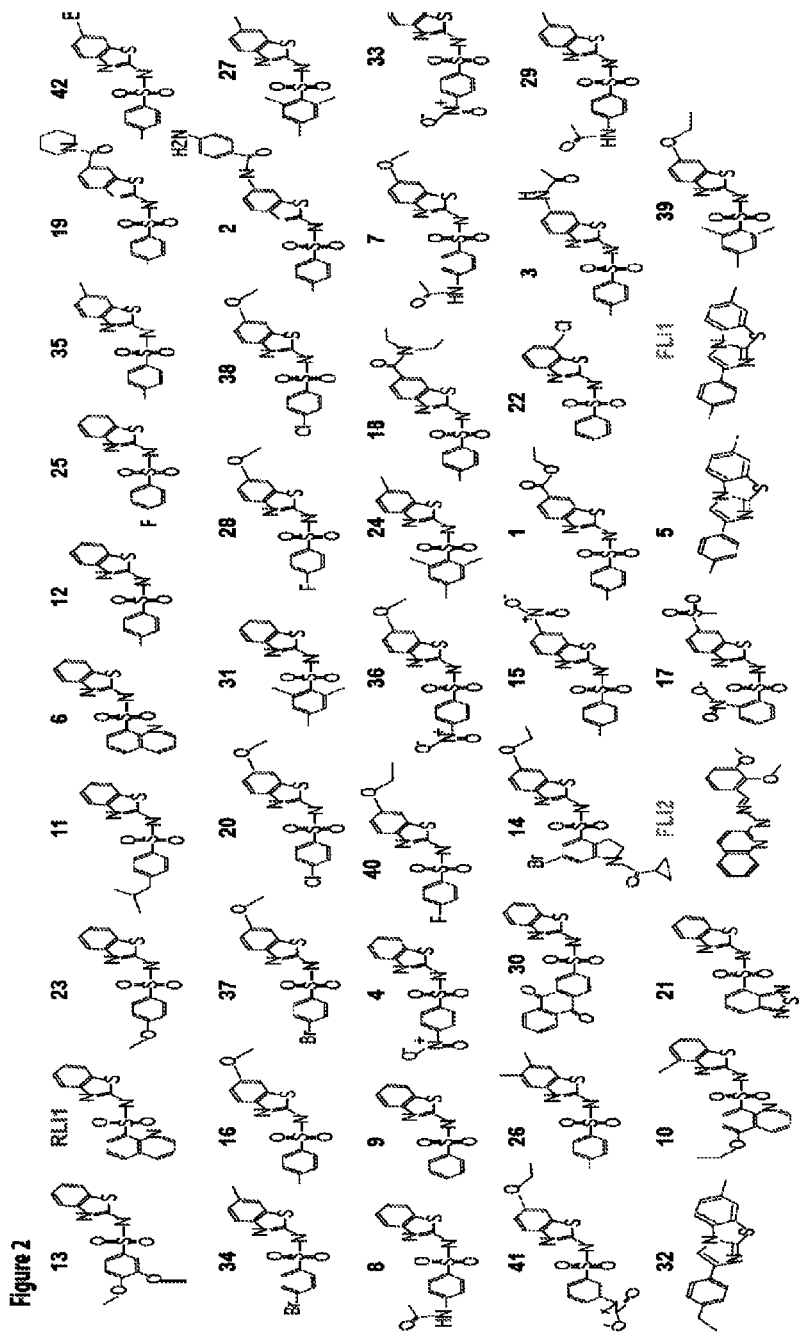
FIG. 2. Analysis of FLIs and RLI specificity and Identification of second generation RL inhibitors with specificity for RL activity. Chemical structures of FLI- and RLI-related compounds tested in vitro for *Renilla*, firefly, Guassia, and *Cypridina* luciferase activity (RLuc, FLuc, GLuc, and CLuc activity, respectively). Note that RLI has both RLuc and FLuc inhibitory activity (henceforth called RLFLI) whereas other compounds tested have either FLuc or RLuc inhibitory activity alone. No inhibitors of GLuc or CLuc were identified from this approach.
Figure 2:
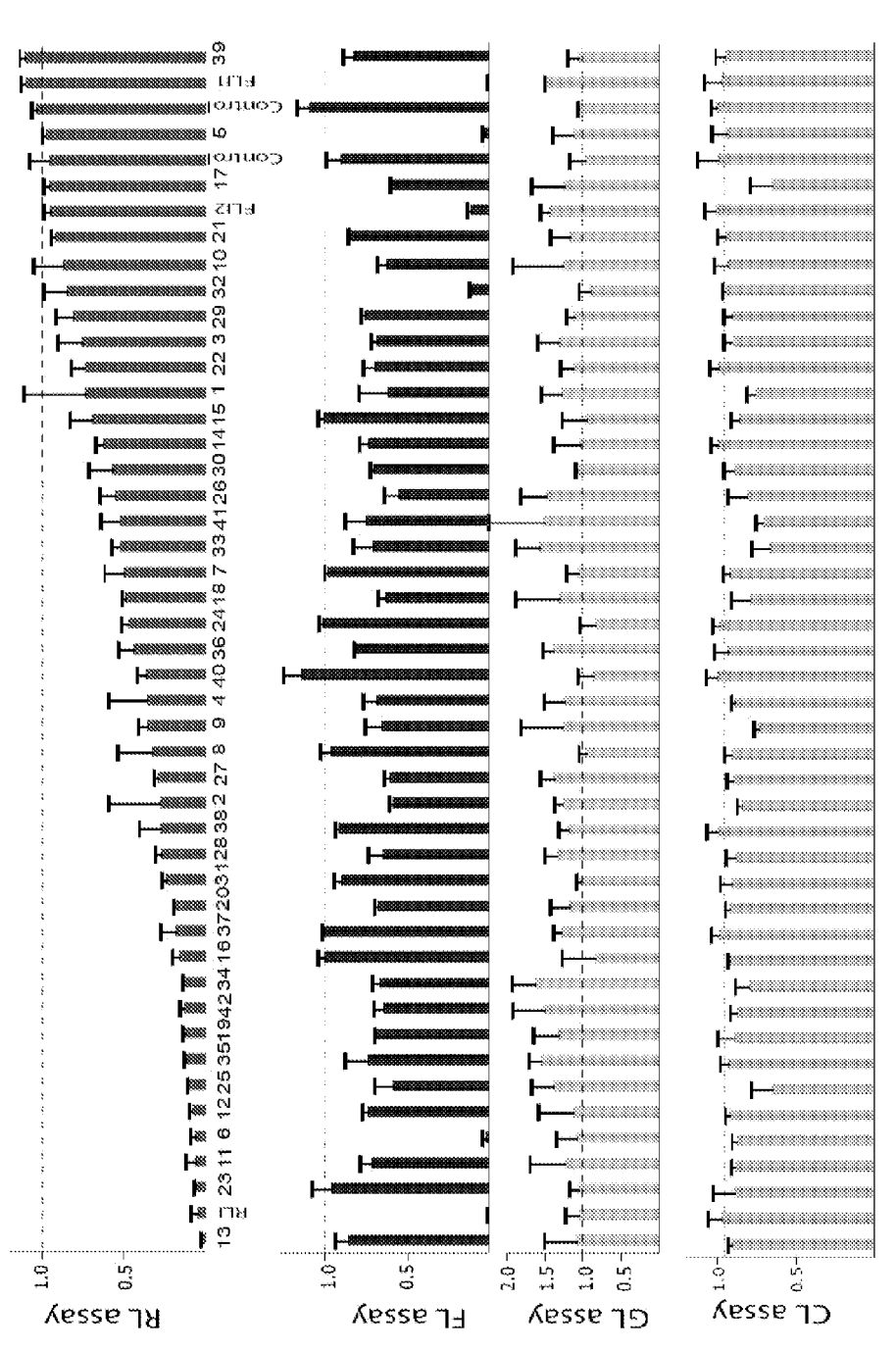
Figure 3:
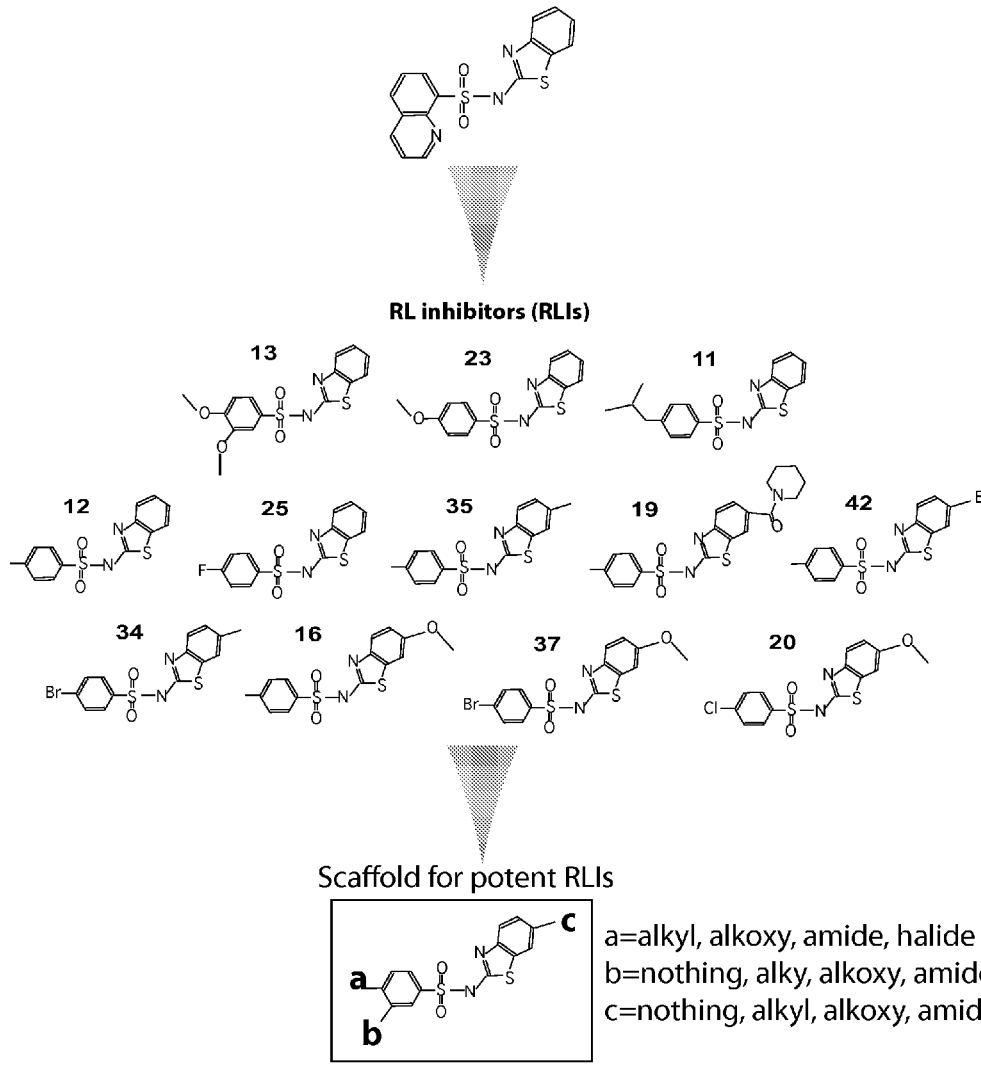
FIG. 3A-B. Assembling a chemical scaffold that supports specific RL and FL inhibitory activity. Compounds related to RLFLI that inhibited RL (FIG. 3A) activity greater than 20% of control and with no activity against FLuc, GLuc, or CLuc, are shown. A general scaffold that supports specific RLuc inhibitory activity emerges.

In accordance with the present invention, a variety of luciferase inhibitors are now provided. As shown in FIG. 2, a number of inhibitors have been tested and can be used in accordance with the present invention to inhibit firefly luciferase, *renilla* luciferase or both. FIG. 3 shows one of the inhibitors from FIG. 2, which is a cross-inhibitor, and a number of additional inhibitors that are specific or selective for *renilla* luciferase, as well as a generic structure indicating the core for such inhibitors.

A. Firefly Luciferase

Firefly luciferase selective inhibitors are identified as compounds 32, FLI1 (also named compound 5), and FLI2. A scaffold for such compounds is shown below and in FIG. 3:

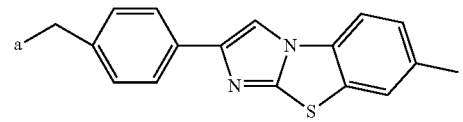

wherein a is H, alkyl substituted or unsubstituted ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide.

B. *Renilla* Luciferase

*Renilla* luciferase selective inhibitors are identified as compounds 13, 23, 11, 12, 25, 35, 19, 42, 34, 16, 37 and 20. A scaffold for such compounds is shown below and in FIG. 3:

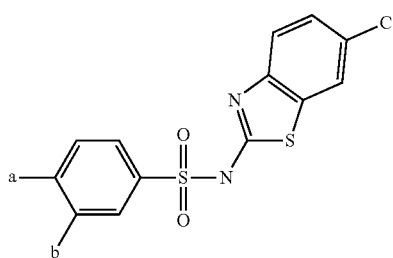

wherein a is H, substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide, wherein b is H, substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide, and c is H, substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide.

C. Cross-Inhibitors

An inhibitor effective on both *renilla* and firefly luciferase are identified as compound RFLI/6.

IV. ASSAY COMPONENTS

A. Expression Constructs

The present invention may involve using expression constructs to luciferase molecules in the context of screening assays. In certain embodiments, it is contemplated that the expression construct comprises nucleic acid sequences encoding luciferase polypeptides, as discussed above. Generally, such methods involve the generation of expression constructs containing, for example, a heterologous nucleic acid sequence encoding the luciferase and a means for its expression, replicating the vector in an appropriate cell.

Luciferase enzymes may be fused to proteins of interest in order to interrogate changes in the proteins' half-lives in response to various cellular perturbations including addition of signaling proteins (such as Wnt, Hh, FGF proteins), chemicals, or siRNAs. Luciferase-fusion proteins co-expressed in cells by introduction of appropriate expression constructs could also be used to examine protein-protein interactions, when a specific protein of interest is immunoprecipitated or otherwise isolated from cells expressing multiple luciferase-fusion proteins and co-purified luciferase activities measured as a determinant of interaction between luciferase-fusion proteins and the target protein.

Yet further, in certain embodiments, it is contemplated that nucleic acid or proteinaceous sequences may be co-expressed with other selected nucleic acid or proteinaceous sequences in the same host cell. Co-expression may be achieved by co-transfecting the host cell with two or more distinct recombinant vectors. Alternatively, a single recombinant vector may be constructed to include fused coding regions for luciferase and other products.

1. Regulatory Sequences

As used in the present invention, the term "expression vector" refers to any type of genetic construct comprising a nucleic acid sequence coding for luciferase polypeptides. In some cases, DNA molecules are then translated into a protein, polypeptide, or peptide. Expression vectors can contain a variety of "control sequences," which refer to nucleic acid sequences necessary for the transcription and possibly translation of an operably linked coding sequence in a particular host cell.

In certain embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase. Much of the thinking about how promoters are organized derives from analyses of several viral promoters, including those for the HSV thymidine kinase (tk) and SV40 early transcription units, or from the cytomegalovirus (CMV). These studies, augmented by more recent work, have shown that promoters are composed of discrete functional modules, each consisting of approximately 7-20 bp of DNA, and containing one or more recognition sites for transcriptional activator or repressor proteins. Other promoters that can be used, include IPTG-inducible promoter.

At least one module in each promoter functions to position the start site for RNA synthesis. The best known example of this is the TATA box, but in some promoters lacking a TATA box.

In the bacterial genome, there are several conserved features in a bacterial promoter: the start site or point, the 10-35 bp sequence upstream of the start site, and the distance between the 10-35 bp sequences upstream of the start site. The start point is usually (90% of the time) a purine. Upstream of the start site is a 6 bp region that is recognizable in most promoters. The distance varies from 9-18 bp upstream of the start site, however, the consensus sequence is TATAAT. Another conserved hexamer is centered at 35 bp upstream of the start site. This consensus sequence is TTGACA. Additional promoter elements regulate the frequency of transcriptional initiation. The spacing between promoter elements frequently is flexible, so that promoter function is preserved when elements are inverted or moved relative to one another.

By employing a promoter with well-known properties, the level and pattern of expression of the protein of interest following transfection or transformation can be optimized or assessed. Further, selection of a promoter that is regulated in response to specific physiologic signals can permit inducible expression of the gene product. In certain embodiments, the promoter will be selected based on an interest in the regulation of a coding sequence naturally associated with the promoter, and the ability of candidate substance to alter the activity of that promoter, once linked to a luciferase coding region, will be assessed.

In certain embodiments of the invention, the cells contain expression cassettes of the present invention, a cell may be selected using a selectable marker in the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

In addition to control sequences that govern transcription and translation, vectors and expression vectors may contain nucleic acid sequences that serve other functions such as replications of origin, transcription termination signals, multipurpose cloning sites, internal ribosome entry site, etc. It is contemplated in the present invention, that virtually any type of vector may be employed in any known or later discovered method to deliver nucleic acids encoding a luciferase polypeptide. Where incorporation into an expression vector is desired, the nucleic acid luciferase polypeptides may also comprise a natural intron or an intron derived from another gene. Such vectors may be viral or non-viral vectors as described herein, and as known to those skilled in the art.

2. Vectors

In particular embodiments of the invention, a plasmid vector is contemplated for use to transform a host cell. In general, plasmid vectors containing replicon and control sequences that are derived from species compatible with the host cell are used in connection with these hosts. The vector ordinarily carries a replication site, as well as marking sequences that are capable of providing phenotypic selection in transformed cells. Plasmid vectors are well known and are commercially available. Such vectors include, but are not limited to, pWL-NEO, pSV2CAT, pOG44, PXT1, pSG (Stratagene) pSVK3, pBSK, pBR322, pcDNA3 and pUC vectors.

Yet further, prokaryote-based systems can be employed for use with the present invention to produce nucleic acid sequences, or their cognate polypeptides, proteins and peptides. Many such systems are commercially and widely available. One skilled in the art is aware of the various prokaryote-based expression systems. Exemplary systems from PROMEGA include, but are not limited to, pGEMEX®-1 vector, pGEMX®-2 Vector, and Pinpoint control Vectors. Examples from STRATAGENE® include, but are not limited to, pBK Phagemid Vector, which is inducible by IPTG, pSPUTK In vitro Translation Vector, pET Expression systems, Epicurian Coli® BL21 Competent Cells and pDual™ Expression System.

3. Transfection/Transformation

In order to effect expression of constructs, the expression construct must be delivered into a cell. This delivery may be accomplished in vitro, as in laboratory procedures for transforming cells lines using well developed procedures. Transformation of cell lines can be achieved using a variety of techniques, although the techniques generally fall into either viral or non-viral methods. These techniques and modifications are well known in the art. Thus, it is well within the scope of the present invention that a cell line may be transformed by any available transformation procedure or modification thereof.

Once the cell is transformed with the vector, the cells are cultured such that the cells multiply resulting in production of the desired protein. In certain embodiments, the cells that are transformed can be bacterial cells. Thus, a skilled artisan is cognizant that the development of microorganisms in culture media is dependent upon a number of very important factors, e.g., the proper nutrients must be available; oxygen or other gases must be available as required; a certain degree of moisture is necessary; the media must be of the proper reaction; proper temperature relations must prevail; the media must be sterile; and contamination must be prevented.

A satisfactory microbiological culture contains available sources of hydrogen donors and acceptors, carbon, nitrogen, sulfur, phosphorus, inorganic salts, and, in certain cases, vitamins or other growth promoting substances. The addition of peptone provides a readily available source of nitrogen and carbon. Furthermore, different media results in different growth rates and different stationary phase densities. A rich media results in a short doubling time and higher cell density at a stationary phase. Minimal media results in slow growth and low final cell densities. Efficient agitation and aeration increases final cell densities. A skilled artisan will be able to determine which type of media is best suited to culture a specific type of microorganism. For example, since 1927, the DIFCO manual has been used in the art as a guide for culture media and nutritive agents for microbiology.

Non-viral Methods. Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736, 524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464, 765, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

In certain embodiments, a nucleic acid may be delivered to an organelle, a cell, a tissue or an organism via one or more injections (i.e., a needle injection), such as, for example, either subcutaneously, intradermally, intramuscularly, intervenously or intraperitoneally. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985).

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw and Hall, 1991), maize (Bhattacharjee et al., 1997), wheat (He et al., 1994) and tomato (Tsukada, 1989).

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, a nucleic acid is delivered into a cell using DEAE-dextran followed by polyethylene glycol. In this manner, reporter plasmids were introduced into mouse myeloma and erythroleukemia cells (Gopal, 1985).

Additional embodiments of the present invention include the introduction of a nucleic acid by direct sonic loading. LTK$^-$ fibroblasts have been transfected with the thymidine kinase gene by sonication loading (Fechheimer et al., 1987).

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramido, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

Viral delivery. The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simplex virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670,488). The various viral vectors described below, present specific advantages and disadvantages, depending on the particular gene-therapeutic application.

In particular embodiments, an adenoviral expression vector is contemplated for the delivery of expression constructs. Adenoviruses comprise linear, double-stranded DNA, with a genome ranging from 30 to 35 kb in size (Reddy et al., 1998; Morrison et al., 1997; Chillon et al., 1999). An adenovirus expression vector according to the present invention comprises a genetically engineered form of the adenovirus. Advantages of adenoviral gene transfer include the ability to infect a wide variety of cell types, including non-dividing cells, a mid-sized genome, ease of manipulation, high infectivity and the ability to be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

A common approach for generating an adenoviruses for use as a gene transfer vector is the deletion of the E1 gene (Er), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1$^-$, replication-deficient virus is then proliferated in a "helper" cell line that provides the E1 polypeptides in trans (e.g., the human embryonic kidney cell line 293). Thus, in the present invention it may be convenient to introduce the transforming construct at the position from which the E1-coding sequences have been removed. However, the position of insertion of the construct within the adenovirus sequences is not critical to the invention. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. Nos. 5,670,488; 5,932,210, each specifically incorporated herein by reference).

In certain embodiments of the invention, the use of retroviruses for gene delivery are contemplated. Retroviruses are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

A recombinant retrovirus of the present invention may be genetically modified in such a way that some of the structural, infectious genes of the native virus have been removed and replaced instead with a nucleic acid sequence to be delivered to a target cell (U.S. Pat. Nos. 5,858,744; 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present invention are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, the gene encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

Herpes simplex virus (HSV) type I and type II contain a double-stranded, linear DNA genome of approximately 150 kb, encoding 70-80 genes. Wild type HSV are able to infect cells lytically and to establish latency in certain cell types (e.g., neurons). Similar to adenovirus, HSV also can infect a variety of cell types including muscle (Yeung et al., 1999), ear (Derby et al., 1999), eye (Kaufman et al., 1999), tumors (Yoon et al., 1999; Howard et al., 1999), lung (Kohut et al., 1998), neuronal (Gamido et al., 1999; Lachmann and Efstathiou, 1999), liver (Miyatake et al., 1999; Kooby et al., 1999) and pancreatic islets (Rabinovitch et al., 1999).

For use in therapeutic gene delivery, HSV must be rendered replication-defective. Protocols for generating replication-defective HSV helper virus-free cell lines have been described (U.S. Pat. Nos. 5,879,934; 5,851,826, each specifically incorporated herein by reference in its entirety). One IE protein, Infected Cell Polypeptide 4 (ICP4), also known as alpha 4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22 and ICP47 (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV cytotoxicity and prevented early and late viral gene expression (Krisky et al., 1998b).

Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions which lends itself to production, storage and transportation requirements.

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Other viral vectors such as poxvirus; e.g., vaccinia virus (Gnant et al., 1999; Gnant et al., 1999), alpha virus; e.g., sindbis virus, Semliki forest virus (Lundstrom, 1999), reovirus (Coffey et al., 1998) and influenza A virus (Neumann et al., 1999) are contemplated for use in the present invention and may be selected according to the requisite properties of the target system.

In certain embodiments, vaccinia viral vectors are contemplated for use in the present invention. Vaccinia virus is a particularly useful eukaryotic viral vector system for expressing heterologous genes. For example, when recombinant vaccinia virus is properly engineered, the proteins are synthesized, processed and transported to the plasma membrane. Vaccinia viruses as gene delivery vectors have recently been demonstrated to transfer genes to human tumor cells, e.g., EMAP-II (Gnant et al., 1999), inner ear (Derby et al., 1999), glioma cells, e.g., p53 (Timiryasova et al., 1999) and various mammalian cells, e.g., P-450 (U.S. Pat. No. 5,506,138). The preparation, growth and manipulation of vaccinia viruses are described in U.S. Pat. Nos. 5,849,304 and 5,506,138 (each specifically incorporated herein by reference).

Chimeric or hybrid viral vectors are being developed for use in therapeutic gene delivery and are contemplated for use in the present invention. Chimeric poxyiral/retroviral vectors (Holzer et al., 1999), adenoviral/retroviral vectors (Feng et al., 1997; Bilbao et al., 1997; Caplen et al., 1999) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of an adenovirus, AAV 5' and 3' ITR sequences and a selected transgene, described below (U.S. Pat. No. 5,871,983, specifically incorporate herein by reference).

B. Host Cells

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, luciferase molecules or a construct thereof. Therefore, recombinant cells are distinguishable from naturally occurring cells that do not contain a recombinantly introduced nucleic acid. In particular embodiments of the present invention, the host cell is a eukaryotic cell that has been transformed with one or more luciferase encoding constructs.

C. Purification of Proteins

In certain embodiments, luciferase proteins may be are expressed using expression systems and may further be purified using standard techniques. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamido gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography.

V. MULTIPLEXED ASSAY FORMATS

A. Transcriptional Reporter Assays

In a first embodiment, the present invention is drawn to transcriptional assays where the luciferase gene is linked to a promoter of interest. When active, the promoter drives transcription of the luciferase mRNA, which is subsequently translated into an active enzyme and activity can be measured. The number of different formats which utilize this basic format are myriad.

One version involves the use of candidates that merely assess their ability to activate pathways upstream of the promoter, such as by increasing or decreasing the amount of transcription factors. Alternatively, the transcriptional readout may be artificial in the sense that the promoter is chosen merely for convenience, and the assay measures another biological event that results in subsequent activation of the promoter. This would include various forms of the "two-hybrid" transcription assay, where the interaction of two molecules is measured by joining each to transcriptional regulatory factors that must act in tandem to promote transcription—in the absence of an interaction, the promoter remains inactive. Many other embodiments exist.

B. Protein-Protein Interaction Assays

Interaction of luciferase fusion proteins can be measured from immunoprecipitation of a target protein from cell lysates expressing additionally expressing interacting proteins fused to various luciferase enzymes.

C. Protein Stability Assays

The levels of several proteins of interest can be monitored by fusing said proteins with luciferase enzymes and monitoring luciferase activities in cells treated with various perturbagens including signaling molecules, small molecules, or siRNAs. Protein stability assays can be also combined with transcription-based reporters using a multiplexed luciferase system.

D. Target Cleavage Assays

The present invention also contemplates assays where the luciferase signal is dependent upon the cleavage of a target molecule by one or more enzymatic agents, such as a protease. In one such format, the luciferase is rendered nonfunctional by inclusion of a protease site that, when cleaved, results in restoration of functionality. One version of this kind of assay involves use of a peptide to circularize the luciferase. Contact with an appropriate protease will result in the linearization of the enzyme, and its subsequent activation.

E. In Vivo Methods

In a further embodiment, the assays of the present invention may be employed in vivo in animals who have cells expressing luciferase molecules. The assays effectively operate as those discussed above, except that the cells must be transformed in vivo or be transgenic (i.e., the luciferase must be integrated into a cell that populates the animal). Such assays find particular use in determining the ability of agents reach a target tissue and to enter target cells, such as cancer cells engineered to express a plurality of luciferases.

VI. KITS

In still further embodiments, the present invention concerns kits for use with the luciferase inhibitors described above. In addition to the inhibitors, one may also include expression constructs encoding various luciferase molecules, as well as cells for expressing the luciferases, either transformed or untransformed with expression constructs. Another component that may be included in the kits is a luciferase substrate. Further suitable reagents for use in the present kits include buffers, diluents, and containers for growing cells, such as flasks or multi-well plates.

The container means of the kits will generally include at least one vial, test tube, flask, bottle, syringe or other container means, into which the reagent may be placed, or preferably, suitably aliquoted. The kits of the present invention will also typically include a means for containing the reagent containers in close confinement for commercial sale. Such containers may include injection or blow-molded plastic containers into which the desired vials are retained.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of RLFLI, FLI, RLI inhibitors. The UTSW 200K chemical library was screened in either L-Wnt-STF cells (Cell line A, Chen et al., 2009) or NIH3T3 cells stably harboring a Hh responsive FLuc reporter and a control RLuc reporter (Cell line B) (FIGS. 1A-B). Compounds that inhibited FLuc activity in L-WNT-STF cells were further tested in cells that express a constitutive FLuc reporter (Cell line C) in order to distinguish between compounds with activity against the Wnt/β-catenin pathway and potential FLuc inhibitors. Two candidate FLuc inhibitors (FLI 1 and 2) were identified (FIG. 1C). Candidate RLuc inhibitors was identified by considering the results from screening both cell lines A and B. Candidate RLuc inhibitors were further tested using lysate from cells expressing RLuc.

Example 2

Candidate FL and RL inhibitors exhibit potent activity in vitro. The two FLIs and one RLI are able to inhibit FLuc and RLuc activity, respectively, in the low μM range (FIG. 1C).

Example 3

Identification of Rluc inhibitors with no activity against FLuc, RLuc, or GLuc. Compounds structurally similar to RLI1 or FLI1 were identified from the UTSW chemical library and tested for inhibitor activity against RLuc, FLuc, GLuc, and CLuc in lysate derived from cells transfected with the corresponding DNA reporter construct (FIG. 2). RLI1 exhibited activity against FLuc (henceforth RLFLI) but many other variants exhibited activity only against RLuc activity and not FLuc. None of the new RLIs exhibited activity against GLuc or CLuc. An additional FLI with similarity to FLI1 was also identified from this exercise (compound 32).

Example 4

A chemical scaffold for inhibitors of RLuc with little activity against other luciferase enzymes identified from compounds with similarity to RLFLI (FIG. 3).

Example 5

Figure 4:
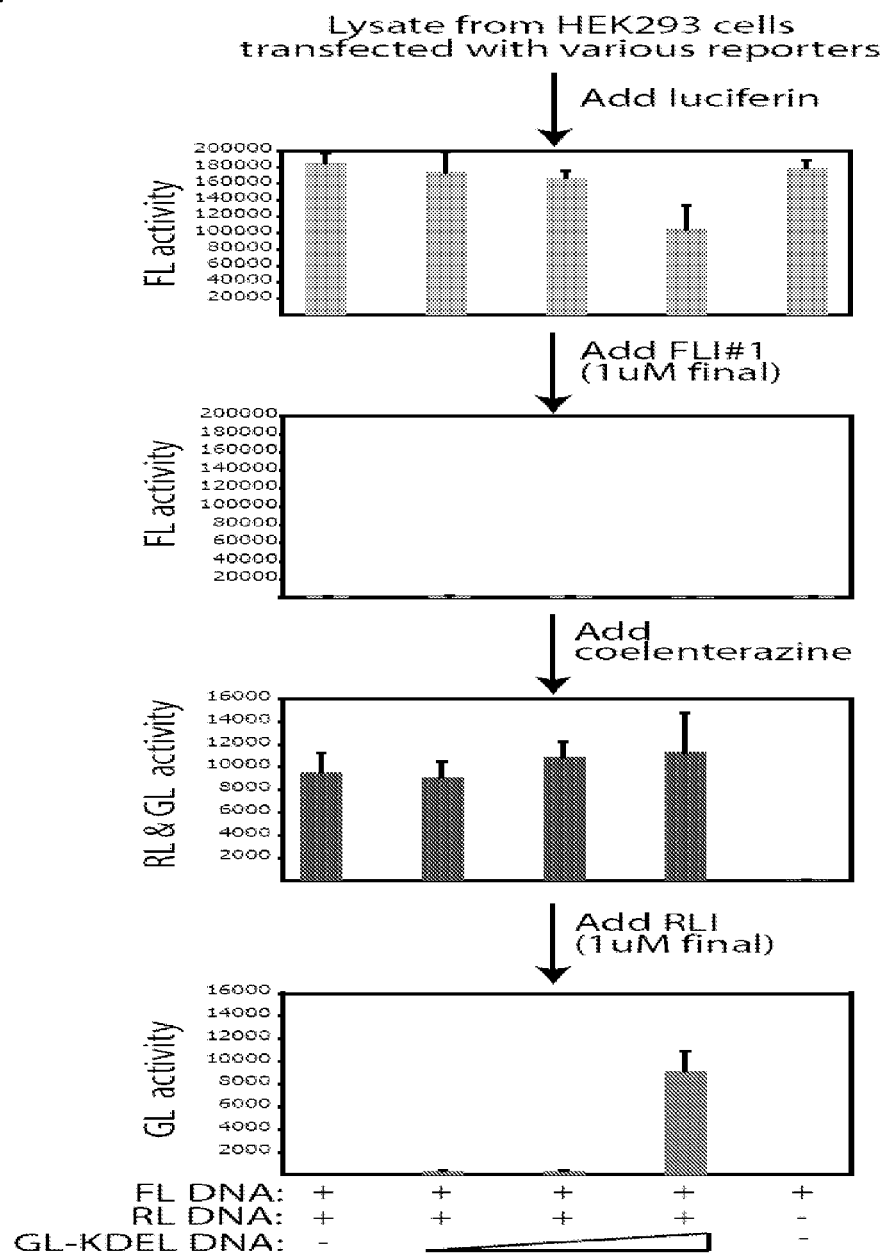
FIG. 4. A multiplexed screening platform premised upon sequential analysis of multiple luciferase-based read-outs. HEK293 cells transfected with indicated FLuc, RLuc or GLuc-KDEL reporters driven by a CMV promoter were lysed and luciferase activities analyzed with the following sequence of addition for substrate and inhibitors: 1) luciferin, 2) FLI1, 3) coelenterazine (reveals both RLuc and GLuc activities), and 4) an RLI (to reveal GLuc signal). GL-KDEL protein is a secreted protein but harbors an endoplasmic reticulum retention signal and is therefore found in the cell lysate as opposed to the culture medium.

FLI and RLI can be used to facilitate multiplexing of luciferase-based assays (FIGS. 4 and 5).

Example 6

Prophetic

Methods. Human cervical carcinoma cells (HeLa cells) are transiently transfected with a Wnt/β-catenin pathway responsive Fluc reporter, a p53 responsive RLuc reporter, a K-ras pathway responsive GLuc-KDEL reporter, and a constitutively expressed secreted Cluc reporter as a control where the ratio of RLuc to GLuc DNA transfected is 5:1. One day post-transfection, transfected cells are split into 96 well culture plates and 94 individual chemicals from a diverse synthetical chemial library added per well. Two wells are reserved for addition of chemical carrier (in this case DMSO) alone. Two days post-addition of chemicals, culture medium is replica-plated in a white-opaque 96 well plate. Remaining cells are washed and lysed in passive lysis buffer. Luciferin is added and FLuc activity (reflecting Wnt/β-catenin pathway activity) measured using a standard luminometer with plate-reading capacity. FL1 is added to quench the Fluc activity prior to addition of coelenterazine to measure both RLuc and GLuc activities (reflecting p53 and Kras pathway activity respectively). Given that the ratio of Rluc to Gluc based reporter is 5:1, luciferase signal detected using coelenterazine predominantly measures Rluc activity. RL1 is added to lysate to quench RLuc activity and to evaluate Gluc activity alone. Cluc activity in the culture medium is analyzed with the addition of *Cypridina* luciferin.

Results. The effects of any invidual compound on Wnt/β-catenin, p53, or K-ras pathway activities will be determined as follows. Datasets for a particular luciferase activity are normalized to controls (lysate from cells treated only DMSO). Chemicals that either inhibit protein secretion or induce cellular toxicity based on loss of CLuc activity in culture medium are eliminated from further consideration. Chemicals that inhibit or augment activity of any particular pathway can be determined by considering the effects of that compound on each luciferase activity. Alternatively, compounds with multiple activities against these pathways can be identified with the same type of analysis.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,684,611
U.S. Pat. No. 4,952,500
U.S. Pat. No. 5,302,523
U.S. Pat. No. 5,322,783
U.S. Pat. No. 5,384,253
U.S. Pat. No. 5,464,765
U.S. Pat. No. 5,506,138
U.S. Pat. No. 5,506,138
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,610,042
U.S. Pat. No. 5,656,610
U.S. Pat. No. 5,670,488
U.S. Pat. No. 5,702,932
U.S. Pat. No. 5,736,524
U.S. Pat. No. 5,739,018
U.S. Pat. No. 5,780,448
U.S. Pat. No. 5,789,215
U.S. Pat. No. 5,849,304
U.S. Pat. No. 5,851,826
U.S. Pat. No. 5,858,744
U.S. Pat. No. 5,871,982
U.S. Pat. No. 5,871,983
U.S. Pat. No. 5,879,934
U.S. Pat. No. 5,932,210
U.S. Pat. No. 5,945,100
U.S. Pat. No. 5,981,274
U.S. Pat. No. 5,994,624
Bates, *Mol. Biotechnol.*, 2(2):135-145, 1994.
Battraw and Hall, *Theor. App. Genet.*, 82(2):161-168, 1991.
Bett et al., *J. Virololgy*, 67(10):5911-5921, 1993.
Bhattacharjee et al., *J. Plant Bioch. Biotech.*, 6(2):69-73, 1997.
Bilbao et al., *FASEB J.*, 11(8):624-634, 1997.
Capaldi et al., *Biochem. Biophys. Res. Comm.*, 74(2):425-433, 1977.
Caplen et al., *Gene Ther.*, 6(3):454-459, 1999.
Chen and Okayama, *Mol. Cell Biol.*, 7(8):2745-2752, 1987.
Chen et al., *Nat. Chem. Biol.*, 5(2):100-107, 2009.
Chillon et al., *J. Virol.*, 73(3):2537-2540, 1999.
Christou et al., *Proc. Natl. Acad. Sci. USA*, 84(12):3962-3966, 1987.
Coffey et al., *Science*, 282(5392):1332-1334, 1998.
D'Halluin et al., *Plant Cell*, 4(12):1495-1505, 1992.
DeLuca et al., *J. Virol.*, 56(2):558-570, 1985.
Derby et al., *Hear Res*, 134(1-2):1-8, 1999.
European Appln. EPO 0273085
Fechheimer et al., *Proc Natl. Acad. Sci. USA*, 84:8463-8467, 1987.
Feng et al., *Nat. Biotechnol.*, 15(9):866-870, 1997.
Fisher et al., *Hum. Gene Ther.*, 7(17):2079-2087, 1996.
Fraley et al., *Proc. Natl. Acad. Sci. USA*, 76:3348-3352, 1979.
Garrido et al., *J. Neurovirol.*, 5(3):280-288, 1999.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gnant et al., *Cancer Res.*, 59(14):3396-403, 1999.
Gnant et al., *J. Natl. Cancer Inst.*, 91(20):1744-1750, 1999.
Gopal, *Mol. Cell Biol.*, 5:1188-1190, 1985.
Graham and Prevec, *Mol Biotechnol*, 3(3):207-220, 1995.
Graham and Van Der Eb, *Virology*, 52:456-467, 1973.
Harland and Weintraub, *J. Cell Biol.*, 101(3):1094-1099, 1985.
He et al., *Plant Cell Reports*, 14 (2-3):192-196, 1994.
Holzer et al. *Virology*, 253(1):107-114, 1999.
Hou and Lin, *Plant Physiology*, 111:166, 1996.
Howard et al., *Ann. NY Acad. Sci.*, 880:352-365, 1999.
Imai et al., *Nephrologie*, 19(7):397-402, 1998.
Kaeppler et al., *Plant Cell Rep.*, 8:415-418, 1990.
Kaneda et al., *Science*, 243:375-378, 1989.
Kato et al, *J. Biol. Chem.*, 266:3361-3364, 1991.
Kaufman et al., *Arch. Ophthalmol.*, 117(7):925-928, 1999.
Kohut et al., *Am. J. Physiol.*, 275(6Pt1):L1089-1094, 1998.
Kooby et al., *FASEB J*, 13(11):1325-34, 1999.
Krisky et al., *Gene Ther*, 5(11):1517-1530, 1998a.
Krisky et al., *Gene Ther*, 5(12):1593-1603, 1998b.
Lachmann and Efstathiou, *Curr. Opin. Mol. Ther.*, 1(5):622-632, 1999.
Lazzeri, *Methods Mol. Biol.*, 49:95-106, 1995.
Lee et al., *Environ. Mol. Mutagen.*, 13(1):54-59, 1989.
Lundstrom, *J. Recept Signal Transduct. Res.*, 19(1-4):673-686, 1999.
Marienfeld et al., *Gene Ther.*, 6(6):1101-1113, 1999.
Miyatake et al., *Gene Ther.*, 6:564-572, 1999.
Morrison et al., *J. Gen. Virol.*, 78(Pt 4):873-878, 1997.
Neumann et al., *Proc. Natl. Acad. Sci. USA*, 96(16):9345-9350, 1999.
Nicolau and Sene, *Biochim. Biophys. Acta*, 721:185-190, 1982.
Nicolau et al., *Methods Enzymol.*, 149:157-176, 1987.
Omirulleh et al., *Plant Mol. Biol.*, 21(3):415-428, 1993.
Parks et al., *J. Virol.*, 71(4):3293-8, 1997.
PCT Appln. WO 9217598
PCT Appln. WO 94/09699
PCT Appln. WO 95/06128
Perales et al., *Proc. Natl. Acad. Sci. USA*, 91:4086-4090, 1994.
Potrykus et al., *Mol. Gen. Genet.*, 199(2):169-177, 1985.
Potrykus et al., *Mol. Gen. Genet.*, 199:183-188, 1985.
Potter et al., *Proc. Natl. Acad. Sci. USA*, 81:7161-7165, 1984.
Rabinovitch et al., *Diabetes*, 48(6):1223-1229, 1999.
Reddy et al., *Virology*, 251(2):414-26, 1998.
Rhodes et al., *Methods Mol. Biol.*, 55:121-131, 1995.
Rippe, et al., *Mol. Cell Biol.*, 10:689-695, 1990.
Robbins and Ghivizzani, *Pharmacol Ther*, 80(1):35-47, 1998.
Robbins et al., *Trends Biotechnol.*, 16(1):35-40, 1998.
Timiryasova et al., *Int. J. Oncol.*, 14(5):845-854, 1999.
Tsukada et al., *Plant Cell Physiol.*, 30(4)599-604, 1989.

Tur-Kaspa et al., *Mol. Cell Biol.*, 6:716-718, 1986.
Wagner et al., *Proc. Natl. Acad. Sci. USA* 87(9):3410-3414, 1990.
Wilson, *J. Clin. Invest.*, 98(11):2435, 1996.
Wong et al., *Gene*, 10:87-94, 1980.
Wu and Wu, *Adv. Drug Delivery Rev.*, 12:159-167, 1993.
Wu and Wu, *J. Biol. Chem.*, 262:4429-4432, 1987.
Yeung et al., *Gene Ther.*, 6(9):1536-1544, 1999.
Yoon et al., *J. Gastrointest. Surg.*, 3(1):34-48, 1999.
Zhou et al., *Exp. Hematol*, 21:928-933, 1993.

What is claimed is:

1. A method of detecting a plurality of distinct luciferase molecules comprising:
   (a) providing a plurality of distinct luciferase molecules in combination with substrates therefor, wherein said plurality of distinct luciferase molecules includes at least *renilla* luciferase and firefly luciferase;
   (b) providing a plurality of distinct luciferase inhibitors, at least one of which selectively inhibits *renilla* luciferase and one of which selectively inhibits firefly luciferase molecules;
   (c) sequentially measuring chemiluminescence from said plurality of distinct luciferase molecules prior to and after combination of said plurality of distinct luciferase inhibitors with said plurality of distinct luciferase molecules,
   whereby the addition of said *renilla* luciferase inhibitor permits the detection of chemiluminescence from non-*renilla* luciferase molecules, and the addition of said firefly luciferase inhibitor permits the detection of chemiluminescence from non-firefly luciferase molecules.

2. The method of claim 1, wherein said plurality of distinct luciferase inhibitors are provided sequentially.

3. The method of claim 1, wherein said plurality of distinct luciferase inhibitors are provided simultaneously.

4. The method of claim 1, wherein said plurality of distinct luciferase molecules comprises 2, 3, 4, 5 or 6 distinct luciferase molecules, 5. The method of claim 1, wherein said plurality of distinct luciferase inhibitors comprises 2, 3, or 4 distinct luciferase inhibitors.

6. The method of claim 1, wherein said plurality of distinct luciferase molecules further comprises one or more of gaussia luciferase, *cypridina* luciferase, gaussia luciferase lacking a secretion signal sequence or having an endoplasmic retention sequence, or *cypridina* luciferase lacking a secretion signal sequence or having an endoplasmic retention sequence.

7. The method of claim 1, wherein said plurality of luciferases are expressed from cells in culture.

8. The method of claim 7, further comprising separating said cells from cell medium.

9. The method of claim 8, further comprising disrupting said cells to form a cell lysate.

10. The method of claim 1, wherein said substrates comprise two or all three of D-luciferin, oxyluciferin, and coelenterazine.

11. The method of claim 1. wherein an inhibitor is selective or specific for *renilla* luciferase.

12. The method of claim 11, wherein said inhibitor selective or specific for *renilla* luciferase has the formula:

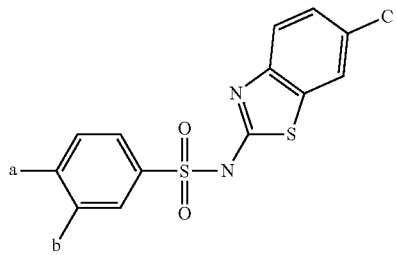

wherein a is substituted or unsubstituted alkyl ($C_1$-$C_{10}$), substituted or unsubstituted alkenyl ($C_1$-$C_{10}$), substituted or unsubstituted alkynyl ($C_1$-$C_{10}$), substituted or unsubstituted alkyoxy ($C_1$-$C_{10}$), amido or halide, b is H, substituted or unsubstituted alkyl ($C_1$-$C_{10}$), substituted or unsubstituted alkyoxy ($C_1$-$C_{10}$), substituted or unsubstituted alkenyl ($C_1$-$C_{10}$), substituted or unsubstituted alkynyl ($C_1$-$C_{10}$), amido or halide, and c is H, substituted or unsubstituted alkyl ($C_1$-$C_{10}$), substituted or unsubstituted alkyoxy ($C_1$-$C_{10}$), substituted or unsubstituted alkenyl ($C_1$-$C_{10}$), substituted or unsubstituted alkynyl ($C_1$-$C_{10}$), amido or halide.

13. The method of claim 1, wherein an inhibitor is cross-reactive with *renilla* luciferase and firefly luciferase.

14. The method of claim 1, wherein an inhibitor is selective or specific for firefly luciferase.

15. The method of claim 14, wherein said inhibitor selective or specific for firefly luciferase has the formula:

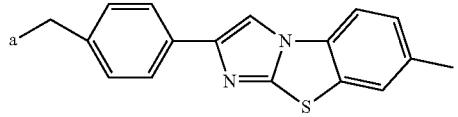

wherein a is H, substituted or unsubstituted alkyl ($C_1$-$C_{10}$), substituted or unsubstituted alkyoxy ($C_1$-$C_{10}$), substituted or unsubstituted alkenyl ($C_1$-$C_{10}$), substituted or unsubstituted alkynyl ($C_1$-$C_{10}$), amido or halide.

16. The method of claim 1, wherein said method comprises measuring firefly lueiferase, *renilla* luciferase, and one or more of gaussia luciferase, *cypridina* luciferase, gaussia luciferase lacking a secretion signal sequence or having an endoplasmic retention sequence, or *cypridina* luciferase lacking a secretion signal sequence or having an endoplasmic retention sequence.

17. The method of claim 1, wherein said method is peformed in an intact cell.

18. The method of claim 1, wherein said method is peformed in a cell-free system.

* * * * *

UNITED STATES PATENT AND TRADEMARK OFFICE
CERTIFICATE OF CORRECTION

| | | |
|---|---|---|
| PATENT NO. | : 8,569,002 B2 | Page 1 of 1 |
| APPLICATION NO. | : 12/908754 | |
| DATED | : October 29, 2013 | |
| INVENTOR(S) | : Lawrence Lum et al. | |

It is certified that error appears in the above-identified patent and that said Letters Patent is hereby corrected as shown below:

In the Claims:

In claim 4, column 27, line 39, delete the "," at end of claim and insert a --.--.

In claim 17, column 28, line 55, delete "peformed" and insert --performed-- therefor.

In claim 18, column 28, line 57, delete "peformed" and insert --performed-- therefor.

Signed and Sealed this
Twenty-fifth Day of February, 2014

Michelle K. Lee
*Deputy Director of the United States Patent and Trademark Office*